United States Patent [19]
Graff et al.

[11] Patent Number: 6,022,699
[45] Date of Patent: Feb. 8, 2000

[54] MYELOPEROXIDASE ASSAY OF ENDOTOXIN-INDUCED INFLAMMATION

[75] Inventors: Gustav Graff, Cleburne; Mark R. Hellberg, Arlington, both of Tex.

[73] Assignee: Alcon Laboratories, Inc., Fort Worth, Tex.

[21] Appl. No.: 09/304,320

[22] Filed: May 3, 1999

Related U.S. Application Data

[60] Provisional application No. 60/086,220, May 21, 1998.

[51] Int. Cl.[7] .............................. C12Q 1/28; C12Q 1/26
[52] U.S. Cl. ................................ 435/28; 435/25
[58] Field of Search ........................ 435/28, 25

[56] References Cited

PUBLICATIONS

Graff et al., J. Pharmacol. Toxicol. Methods 39 (3) 169–178, 1998.
Haugaard et al., Anal. Biochem 116(2): 341–343, 1981.
Nelson et al., Anal Biochem 49: 471–478, 1972.
Baatz et al., Invest Ophthalmol Vis Sci 36: 1960–1967 (1995).
Bhattacherjee et al., Invest Ophthalmol Vis Sci 24: 196–202 (1983).
Bradley et al., J Invest Dermatol 78: 206–209 (1982).
Claiborne et al., Biochemistry 18: 2324–2329 (1979).
Costagliola et al., Exp Eye Res 43: 905–914 (1986).
Cousins et al., Exp Eye Res 39: 665–676 (1984).
Cramer et al., Adv Exp Med Biol 121(A):91–9 (1979).
De Berardinis et al., Exp Eye Res 4: 179–186 (1965).
Egan et al., Agents Actions 29: 266–276 (1980).
Floris et al., Eur J Biochem 207: 697–702 (1992).
Forrester et al., Graefes Arch Klin Exp Ophthalmol 213: 221–233 (1980).
Graff et al., Prostaglandins 38: 473–496 (1989).
Grisham et al., Methods in Enzymology, vol. 186, Ed. Packer et al., San Diego: Academic Press, pp. 729–742 (1990).
Hockwin et al., Glutathione: Metabolism and physiological functions, Ed., Vina, Boca Raton: CRC Press, pp. 207–215 (1990).
Krawisz et al., Gastroenterology 87: 1344–1350 (1984).
Liem et al., Anal Biochem 98: 388–393 (1979).
Marquez et al., J Biol Chem 265: 5666–5670 (1990).
Nelson et al., Anal Biochem 49: 474–478 (1972).
Saxena et al., Exp Eye Res 55: 461–468 (1992).
Schultz et al., Arch Biochem Biophys 96: 465–467 (1962).
Tsuji et al., Exp Eye Res 64: 31–36 (1997).
Udelsman et al., Curr Probl Surg 31: 655–720 (1994).
Varma et al., Ophthalmic Res 20: 164–173 (1988).
Vinegar et al., J Pharmacol Exp Ther 166: 96–103 (1969).
Whitcup et al., Invest Ophthalmol Vis Sci 33:2626–2630 (1992).
Williams et al., Curr Eye Res 2: 465–470 (1982).
Williams et al., Exp Eye Res 39: 261–265 (1984).
Williams et al., Exp Eye Res 42: 211–218 (1986).
Winter et al., Proc Soc Exp Biol Med 111: 544–547 (1962).
Wise et al., Carcinogenesis 5: 1499–1503 (1984).
Wise et al., Carcinogenesis 6: 579–583 (1985).
Worthington Biochemical Corporation (1972) Peroxidase. Worthington Enzyme Manual.

Primary Examiner—Francisco Prats
Assistant Examiner—Susan D. Coe
Attorney, Agent, or Firm—Patrick M. Ryan

[57] ABSTRACT

An improved model of endotoxin-induced inflammation is obtained by eliminating the interference in the biochemical assay of myeloperoxidase caused by endogenous reductants and cellular constituents containing free thiol functional groups. The interference was eliminated by 1) extensively diluting soluble, interfering substances and 2) blocking tissue sulfhydril functional groups during tissue homogenization. The improved model can be used to assess the therapeutic potential of anti-inflammatory agents. For example, the model can be used to evaluate topically administrable ophthalmic anti-inflammatory agents in Lewis rats.

12 Claims, 2 Drawing Sheets

MYELOPEROXIDASE ASSAY OF ENDOTOXIN-INDUCED INFLAMMATION

This application claims priority from co-pending U.S. Provisional Patent Application Serial No. 60/086,220, filed May 21, 1998.

FIELD OF THE INVENTION

This invention relates to in vivo models for identifying anti-inflammatory agents. In particular, this invention relates to a model of endotoxin-induced inflammation for the evaluation of anti-inflammatory agents.

BACKGROUND OF THE INVENTION

Carrageenan-induced paw edema in the rat has been a standard in vivo model for the pharmacological evaluation of systemically administered anti-inflammatory agents. See Winter et al., *Proc Soc Exp Biol Med* 111: 544–547 (1962) and Vinegar et al., *J Pharmacol Exp Ther* 166: 96–103 (1969). In this model, subplantar administration of irritant into the hind paw of the rat causes a local inflammatory response which can be inhibited by steroidal and non-steroidal anti-inflammatory agents.

A related model has been developed by Williams et al., *Curr Eye Res* 2: 465–470 (1982) for the evaluation of topical ocular anti-inflammatory agents. In this model, bacterial endotoxin (LPS) is administered into the vitreous of the rabbit eye, resulting in an inflammation of the uvea characterized by accumulation of neutrophils (PMNs) in ocular tissue. These investigators utilized a biochemical method that allows indirect quantification of tissue-associated PMNs by assessing myeloperoxidase (MPO) activity contained in the azurophilic granules of the cell.

An alternative model of endotoxin-induced uveitis has been established in rats. (See, Forrester et al., *Graefes Arch Klin Exp Ophthalmol* 213: 221–233 (1980) and Bhattacherjee et al., *Invest Ophthalmol Vis Sci* 24: 196–202 (1983)). In this model, PMN influx into ocular tissue following subplantar or intravitreal injection of LPS is quantified by counting stained cells in a known volume of aqueous humor. See, also, Williams et al., *Exp Eye Res* 42: 211–218 (1986) and Tsuji et al., et al., *Exp Eye Res* 64: 31–36 (1997).

Each of the above approaches used to quantify ocular PMN content in models of endotoxin-induced uveitis has inherent shortcomings. Specifically, Bhattacherjee et al., *Invest Ophthalmol Vis Sci* 24: 196–202 (1983) reported considerable disparity in cell counts (as high as 40%) between the eyes of a single test animal when quantifying microscopically stained cells obtained by anterior chamber tap. This approach requires thorough mixing of the aqueous humor to dislodge tissue-adherent leukocytes prior to fluid removal in order to obtain a representative and homogeneous sample. Avidly adherent cells may not be dislodged and, therefore, not quantified by this procedure.

Similarly, the biochemical assessment of PMN-associated MPO activity employed by Williams et al., *Curr Eye Res* 2: 465–470 (1982) has notable deficiencies. Although endotoxin-induced uveitis in rabbits theoretically offers the advantage of providing a relatively large ocular globe, technical issues associated with tissue preparation and subsequent fractionation of large extract volumes make evaluation of total ocular PMN content cumbersome. This approach requires tissue extraction and solubilization of the MPO with hexadecyltrimethylammonium bromide (HTA-Br). See, Bradley et al., *J Invest Dermatol* 78: 206–209 (1982).

Although PMN-derived MPO primarily catalyzes hydrogen peroxide ($H_2O_2$)-dependent oxidation of halides (i.e., chloride ions) physiologically, its ability to use artificial electron donors such as o-dianisidine (o-DA) as substrates has become the basis of the spectrophotometric determination of enzyme activity and a means of quantifying PMNs in inflamed tissue. Modifications of this method have been introduced to circumvent artifacts contributed by tissue/blood constituents, including cytosolic enzymes such as catalase, glutathione peroxidase, and heme proteins, and reducing substrates such as glutathione (GSH) and ascorbic acid (ASC). See, for example, Grisham et al., *Methods in Enzymology*, Vol. 186, Ed. Packer et al., San Diego: Academic Press, pp. 729–742 (1990), Liem et al., *Anal Biochem* 98: 388–393 (1979), and Egan et al., *Agents Actions* 29: 266–276 (1990).

Since the initial report of ocular PMN accumulation in the rabbit model of endotoxin-induced uveitis (Williams et al., *Curr Eye Res* 2: 465–470 (1982)), however, little consideration has been given to the presence of endogenous electron donors that may interfere in the assay of PMN-associated MPO activity. There is a need for a more reliable analytical method of quantifying PMN content of inflamed tissues, one that is not affected by endogenous tissue constituents.

SUMMARY OF THE INVENTION

The present invention relates to a test system for the evaluation of anti-inflammatory agents. Specifically, the test system is an assay of PMN-associated MPO activity in tissues from experimental animals, such as the Lewis rat, challenged with a bacterial endotoxin (LPS). The assay provides reliable PMN determinations by eliminating interference that can be caused by endogenous electron donors such as ASC or thiols, including GSH and protein sulfhydryls.

DETAILED DESCRIPTION OF THE INVENTION

Figure 1:
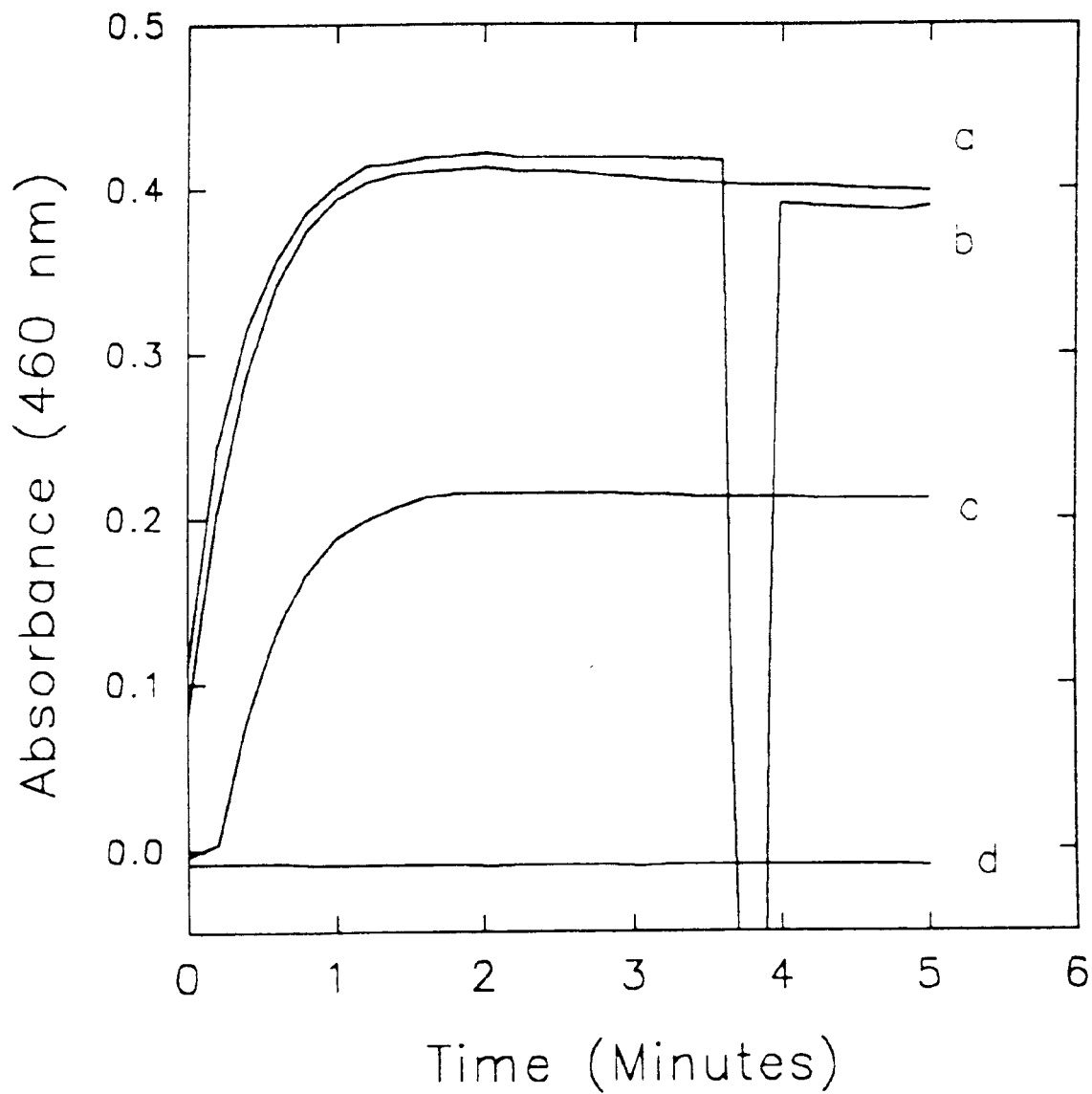
FIG. 1 shows the effect of ASC on MPO-catalyzed oxidation of o-DA.

Vascular leakage and recruitment of circulating PMNs to the site of injury represents the early phase of the host defense mechanism and response to tissue injury. This response is common to all organs and tissues, including the eye. Clinically, the presence of PMNs in the anterior chamber of the eye can be readily detected by slit-lamp examination or quantified with the use of a Kowa cell/flare meter. However, this technology is not particularly useful when quantifying the presence of PMNs in the eyes of experimental species such as the rat. A more quantitative approach is the use of the biochemical assay of PMN-associated MPO activity. This enzyme is highly enriched in the azurophil granules of PMNs (Schultz et al., *Arch Biochem Biophys* 96: 465–467 (1962) recruited to injured tissue to mediate the acute phase of the inflammatory response (Vinegar et al., *J Pharmacol Exp Ther* 166: 96–103 (1969). MPO is not found in normal, non-inflamed tissue.

In the typical enzymatic cycle of peroxidases, native enzyme reacts with $H_2O_2$ to form what is known in the literature as Compound I ($Fe^{v+}=O$), in which the heme group acquires two additional oxidizing equivalents. Compound I recycles back to the native enzyme via two one-electron steps utilizing two reducing substrate molecules which are converted to radicals (Marquez et al, *J Biol Chem* 265: 5666–5670 (1990)). The ability of the enzyme to react with a broad range of reducing co-substrates including o-DA underscores its utility as a marker for the detection and quantification of tissue-associated PMNs. Experimentally, the $H_2O_2$-dependent oxidation of o-DA and its conversion to 3,3'-dimethoxybenzidinediimine is readily monitored spectrophotometrically at 460 nm. However, o-DA oxidation can easily lead to erroneous results of MPO activity if heme proteins or endogenous electron donors (e.g., ASC and GSH) are not effectively removed from tissue extracts. Extracts contaminated with heme proteins cause an overestimation of peroxidase activity due to nonenzymic, pseudo-peroxidase activity (Grisham et al., *Methods in Enzymology*, Vol. 186, Ed. Packer et al., San Diego: Academic Press, pp. 729–742 (1990); Liem et al., Anal *Biochem* 98: 388–393 (1979)). Endogenous reductants, on the other hand, compete with o-DA in the reduction of MPO-Compound I, resulting in an underestimation of peroxidase activity (Marquez et al., *J Biol Chem* 265: 5666–5670 (1990); Grisham et al., *Methods in Enzymology*, Vol. 186, Ed. Packer et al., San Diego: Academic Press, pp. 729–742 (1990); Egan et al., *Agents Actions* 29: 266–276 (1990); Williams et al., *Exp Eye Res* 39: 261–265 (1984)). In addition to competing with o-DA in the reductive regeneration of native peroxidase enzyme, ASC causes the nonenzymic reduction of 3,3'-dimethoxybenzidinediimine to o-DA (Wise et al., *Carcinogenesis* 5: 1499–1503 (1984). Both processes lead to an underestimation of MPO activity.

In contrast to ASC, GSH appears to react with in-situ generated sulfhydryl reactive benzidinediimine to form 3-(glutathion-S-yl)-benzidine which exhibits minimal absorptivity at 460 nm (Wise et al., *Carcinogenesis* 5: 1499–1503 (1984). However, in our studies neither ASC nor GSH affected the absorptivity of uninhibited, ceased enzyme reactions. These observations indicate that, under the assay conditions employed, in-situ generated 3,3'-dimethoxybenzidinediimine dimerized rapidly to the non-reducible/unreactive bisazobiphenyl product (Claiborne et al., *Biochemistry* 18: 2324–2329 (1979). The inhibitory effect of GSH on the oxidative conversion of o-DA to 3,3'-dimethoxybenzidinediimine by MPO can be prevented with a non-interfering thiol reactive compound. "Non-interfering" means that the thiol reactive compounds do not inactivate the enzyme (MPO). Suitable non-interfering thiol reactive compounds include maleimide, N-methyl maleimide, N-ethyl maleimide, ethacrynic acid, and maleic anhydride. A preferred non-interfering thiol reactive compound is N-ethyl maleimide (NEM). NEM does not affect MPO catalysis in the absence of GSH. For convenience only, NEM will be used as a representative non-interfering thiol reactive compound in the remainder of this Detailed Description section. Converting all GSH to 3-(glutathion-S-yl)-succinimide by reaction with an excess of NEM eliminates the reaction between GSH and 3,3'-dimethoxybenzidine-diimine generated during MPO catalysis. This allows for an unimpaired absorbance at 460 nm.

The lack of effect of NEM on MPO was exploited in developing the present endotoxin-induced inflammation model and the assay of PMN-derived MPO activity associated with tissue post-LPS challenge. Although the method of the present invention is applicable to a variety of experimental species, including the Lewis rat, NZA rabbit, DB rabbit and other rabbit strains, the method is preferably conducted with Lewis rats. The present method is capable of application to a variety of target tissues within the chosen experimental species, e.g., ocular, dermatological, intestinal, articular and vascular tissues. A preferred target tissue for the method of the present invention is the ocular tissue. In contrast to other species, rat ocular tissues contain relatively small amounts of ASC. This reductant resides predominantly in the cornea with barely detectable levels in the vitreous (Varma et al., *Ophthalmic Res* 20: 164–173 (1988). The low ASC concentration, its selective association with the cornea, combined with its high aqueous solubility and its extensive dilution during tissue homogenization minimize the potential for interference in the MPO assay. However, GSH, a ubiquitous mammalian cellular constituent, presents a greater potential for assay interference. It is found at a concentration of about 4 mM in the rat lens (Costagliola et al., *Exp Eye Res* 43: 905–914 (1986)), a tissue contributing about 40% to the total ocular mass in this species.

As expected, tissue homogenization with HTA-Br buffer alone allowed detection of only 10% of total tissue MPO activity. MPO specific activity was enhanced substantially (40% of total) when tissue homogenization was conducted per published methods (Grisham et al., *Methods in Enzymology*, Vol. 186, Ed. Packer et al., San Diego: Academic Press, pp. 729–742 (1990)) using a large excess of homogenization buffer in combination with HTA-Br buffer extraction. This finding indicates a partial removal and/or dilution of endogenous reductants/thiols during tissue fractionation. Only upon inclusion of NEM in the homogenization buffer in combination with HTA-Br extraction was maximal recovery of assayable MPO activity achievable following LPS challenge. Blocking free sulfhydryl functional groups (i.e., residual glutathione and protein sulfhydryls) during tissue extraction by reaction with NEM prevents their later reaction with 3,3'-dimethoxybenzidinediimine, and thus prevents underestimation of o-DA oxidation in the MPO assay. Notably, the use of NEM during tissue extraction did not affect the apparent substrate affinities of neutrophil MPO for either $H_2O_2$ or o-DA which were comparable to those determined for the human sputum derived enzyme.

With the elimination of assay interference by endogenous thiols, endotoxin-stimulated PMN influx into ocular tissue in the Lewis rat was re-examined. A single subplantar administration of LPS dose-dependently elicited ocular PMN influx, with a plateau of effect between 100 µg and 200 µg of LPS. The uveitis was bilateral, with less than 15% difference in PMN derived MPO activity observed between companion eyes. The method of the present invention, which in this case has been applied to eye tissue, monitors total ocular MPO activity and has less inherent variability between companion eyes than methods that employ aqueous humor taps combined with cell counting (Bhattacherjee et al., *Invest Ophthalmol Vis Sci* 24: 196–202 (1983)). However, there appears to be considerable variability between animals in total MPO activity. This is likely the result of differences among animals in their endocrine response (glucocorticoid release) to the inflammatory stress condition (Udelsman et al., *Curr Probl Surg* 31: 655–720 (1994)). An alternative, but a less likely cause, may be an inadequate delivery of, or variable pharmacodynamics relative to, subplantarly administered LPS.

As monitored by MPO activity, ocular accumulation of PMNs 24 hours following endotoxin challenge was dose-dependently inhibited by topical ocular administration of dexamethasone ($ED_{50} \approx 0.01\%$). Similar inhibition has been reported for topically administered betamethasone in a rat uveitis model using salmonella endotoxin as inflammatory stimulus (Tsuji et al., *Exp Eye Res* 64: 31–36 (1997)). Histopathologic evaluation confirmed the dose dependent decline in PMNs in both the anterior and posterior compartments and associated ocular tissue of topical dexamethasone-treated animals.

Thus, an effective endotoxin-induced inflammation assay for comparison of the anti-inflammatory efficacy and potency of a drug comprises the steps of:

a) administering (e.g., topically or systemically) the drug therapeutically or prophylactically (or both) to a target tissue of an experimental animal;

b) inducing inflammation in the animal by administration of an endotoxin;

c) isolating the target tissue approximately 16–30 hours, preferably about 24 hours, after administration of the endotoxin;

d) homogenizing the target tissue in a buffered composition comprising a non-interfering thiol reactive compound, wherein the buffered composition has a pH of about 5–8, preferably about pH 7.4;

e) centrifuging the composition of step (d) to recover PMN and MPO in a pellet;

f) solubilizing the pellet of step (e) in a buffered composition containing HTA-Br in order to release MPO from PMN azurophil granules, wherein the buffered composition has a pH of about 5–7, preferably pH 6;

g) centrifuging the composition of step (f) to recover MPO in the supernatant;

h) preparing a buffered composition comprising the supernatant of step (g), o-DA, $H_2O_2$ and HTA-Br, wherein the buffered composition has a pH of about 5–7, preferably about pH 6; and i) determining MPO activity by spectrophotometrically monitoring at about 460 nm change in absorbance of the composition of step (h) due to o-DA oxidation.

In the case where the target tissue is ocular tissue, the method of the present invention preferably involves bilateral administration of the test article (or control). The dosing regimen may be therapeutic (0–about 20 hrs. post-administration of the endotoxin), prophylactic (about 24 hrs. or less prior to administration of the endoxin), or both; for example, a test article can be administered at −24, −6, +1, and +4 hours, relative to the time (t=0) of endotoxin administration.

One suitable buffer for use in the compositions of steps (d) and (f) is phosphate buffer a concentration of 50 mM. The centrifugation steps (e) and (g) should be conducted at low temperatures, e.g., ice-cold temperatures of about 4° C.

The non-interfering thiol reactive compound is preferably NEM. The concentration of non-interfering thiol reactive compound in the composition of step (d) is should be about 0.1–30 mM, preferably about 10 mM. The volume of the composition of step (d) is generally about 10–100 times, preferably about 50 times, the weight of the enucleated eye. For example, assuming that the total weight of the eye tissue is 0.1 g and that 0.1 g is roughly equivalent to 0.1 mL, the volume of the composition of step (d) is preferably 5 mL.

In a preferred embodiment, the method of the present invention comprises two additional steps between step (e) and step (f). The two additional steps are an intermediate extraction/washing step and another centrifugation step. These additional steps (i.e., repetitive extraction/washing) improve the efficiency of recovering MPO from the target tissue. For example, immediately after step (e), the pellet is re-dissolved in a fresh buffered, pH about 5–8, preferably pH about 7.4, composition comprising a non-interfering thiol reactive compound, and then centrifuged again before step (f).

As described by Grisham et al., (*Methods in Enzymology*, Vol. 186, Ed. Packer et al., San Diego: Academic Press, pp. 729–742 (1990)), the HTA-Br step (step (f)) preferably involves three freeze/thaw cycles to help maximize the PMN disruption and release of MPO from azurophil granules. The solubilization of the pellet of step (e) is preferably aided by mechanical means, such as probe sonication.

After the supernatant (containing MPO) is recovered (step(g)), it is combined with o-DA, $H_2O_2$ and HTA-Br in a buffered composition. The rate of o-DA oxidation in the buffered composition is then monitored spectrophotometrically (460 nm) as an indication of the amount of MPO activity. The amount of o-DA to be present in the buffered composition to be assayed should be about 1–1.5 mM, preferably about 1.4–1.5 mM. The amount of $H_2O_2$ to be present in the buffered composition to be assayed should be about 150–300 µM, preferably about 220–300 µM. The amount of HTA-Br present in the buffered composition to be assayed should be about 100–500 µM, preferably about 250 µM.

In order to determine whether observed oxidation of o-DA is attributable to MPO activity or to a non-enzymatic (e.g., heme catalyzed) reaction, the supernatant recovered in step (g) is assayed in two separate reactions both supplemented with o-DA and $H_2O_2$ as described above. One reaction is carried out in the absence and the other in the presence of either a cyanide salt (e.g., KCN), in an amount of about 1–10 mM, preferably about 1 mM, or sodium azide ($NaN_3$), in an amount of about 5–30 mM, preferably about 10 mM. If the rate of o-DA oxidation is much greater in the case of the reaction without a cyanide salt or $NaN_3$, the o-DA oxidation is attributable to MPO activity. With the method of the present invention, there should be less than about 5% non-enzymatic oxidation of o-DA.

The invention will be further illustrated by the following examples which are intended to be illustrative, but not limiting.

EXAMPLES

Reagents

N-ethylmaleimide (NEM), o-DA (3,3'-dimethoxybenzidine dihydrochloride), HTA-Br, LPS (lipopolysaccharide, *E. coli* 0111:B4), heparin, dexamethasone, histopaque 1083 and histopaque 1119 were obtained from Sigma Chemical Company, St. Louis, Mo. Dextran-100 was a product of Crescent Chemical Company, Hauppauge, N.Y. Hydrogen peroxide (30%) was obtained from J. T. Baker and stored at 4° C. All other chemicals used were of the highest purity available. Human sputum myeloperoxidase (HSMPO) was obtained from Elastin Products Co., Pacific, Mo. The enzyme (2.4 mg solid) was dissolved in 2.4 mL of 50 mM potassium phosphate buffer (pH 6.0), and stored in 0.1 mL aliquots at −20° C., then diluted 10-fold with 50 mM potassium phosphate buffer (pH 6.0) to provide a HSMPO concentration of 0.1 mg/mL.

Induction of Uveitis

Uveitis was induced by subplantar injection of 0.1 mL of a saline solution containing 200 µg of LPS into the right hind paw of female Lewis rats (4 to 5 animals/group). Twenty-four (24) hours after LPS injection, animals were sacrificed by $CO_2$ inhalation, and total ocular PMN content was determined by assessing MPO activity, as described below.

Ocular Tissue Preparation

Ocular tissues were prepared for the quantification of PMN content as follows. Freshly enucleated eyes, or eyes rapidly frozen on dry ice and stored at −70° C. were homogenized in 5.0 mL of ice-cold buffer with the aid of a Brinkman Polytron homogenizer. The homogenizer probe was rinsed with 5.0 mL of the same buffer, and washings were combined with the initial tissue homogenate. The homogenate was centrifuged for 30 minutes at 12,000×g at 4° C. The proteinaceous pellet was then homogenized once more in ice-cold buffer and the homogenate was centrifuged again (as described above). The supernatant, devoid of MPO activity, was discarded and the proteinaceous pellet was solubilized in either 0.5 mL or 1.0 mL of ice-cold 0.5% hexadecyltrimethylammonium bromide (HTA-Br)/50 mM phosphate buffer (pH 6.0) (HTA-Br buffer) as indicated. Solubilization was accomplished using a probe-type sonicator (three 10-second bursts from a Heat Systems, Inc. Ultrasonic Process sonicator, Model XL-2010, at an instrument power setting of 2) followed by three sequential freeze (dry ice)-thaw cycles. The HTA-Br buffer-treated pellet homogenate was centrifuged (4° C., 30 minutes 12,000×g). The supernatant was collected, frozen and stored at −70° C. for later assay of MPO activity.

Assessment of MPO Activity

The MPO activity of the ocular tissue extracts was determined by continually monitoring the change in absorbance (Beckman DU-65 spectrophotometer) of MPO reactions at 460 nm for a period of three minutes in the presence of specified concentrations of $H_2O_2$ and o-DA. Initial rates of enzyme activity were determined from changes in optical density occurring within the first minute of reaction. Optical density units were converted into units of concentration using the molar absorptivity coefficient for oxidized o-DA ($e=10,062 \times (M \times cm)^{-1}$). Assays were conducted at room temperature in a final total volume of 1.5 mL. The reaction buffer contained 50 mM phosphate/250 $\mu$M HTA-Br/300 $\mu$M $H_2O_2$ and 1.5 mM o-DA (pH 6.0). Reactions were initiated by addition of an appropriate amount of HTA-Br solubilized ocular tissue extract. $H_2O_2$ concentration was determined spectrophotometrically at 240 nm. See, Nelson et al., Anal. Biochem., 49: 474–478 (1972).

Evaluation of Topical Ocular Anti-inflammatory Agents

Inhibition of PMN influx into ocular tissue of the Lewis rat by dexamethasone was evaluated as follows. Dexamethasone suspensions were prepared in a carbopol ophthalmic suspension vehicle at concentrations of 0.0033%, 0.01%, 0.033%, 0.04% and 0.10%, w/v. A 5 $\mu$L aliquot of test drug or vehicle was applied topically to each eye of the experimental animals 24, 20, and 4 hours prior to, at the time of, and 4 and 20 hours after LPS foot pad injection. Twenty-four (24) hours following LPS administration, eyes were enucleated, quickly frozen on dry ice and stored at −70° C. until used for tissue extraction and assessment of MPO activity. Alternatively, eyes were enucleated and fixed in a solution of phosphate buffered (40 mM) formalin (4%), pH 6.0. Eyes were embedded in paraffin and sectioned. Using light microscopy, hematoxylin- and eosin-stained sections were examined for the presence and distribution of PMN infiltrates within the different compartments of the eye. Infiltrates were ranked subjectively on a scale ranging from 0 to 5, where 0=not remarkable, 1=minimal, 2=slight/mild, 3=moderate, 4=moderately severe, and 5=severe/high.

Example 1

HSMPO was used as reference to assess the enzyme's substrate dependence on both $H_2O_2$ and o-DA. As shown in Table 1, optimal reaction rates were obtained in the presence of 300 $\mu$M $H_2O_2$ and 1.5 mM o-DA. However, substrate saturation conditions could not be attained for o-DA since precipitates formed at concentrations exceeding 1.5 mM. $H_2O_2$ concentrations greater than 300 $\mu$M resulted in a loss of enzyme activity. This loss of activity was likely the result of peroxide-induced heme bleaching (see, Floris et al., Eur J Biochem 207: 697–702 (1992)) due to a limiting concentration of o-DA.

TABLE 1

Kinetics$^\Psi$ of HSMPO

| $H_2O_2$ Concentration ($\mu$M) | Reaction Velocity^ ($\mu$M/min/$\mu$g) | o-DA Concentration (mM) | Reaction Velocity⊥ ($\mu$M/min/$\mu$g) |
|---|---|---|---|
| 0 | 0 | 0 | 0 |
| 13 | 2.7 | 0.097 | 1.6 |
| 27 | 6.4 | 0.25 | 4.2 |
| 54 | 9.6 | 0.49 | 8.0 |
| 107 | 14.2 | 0.97 | 16.3 |
| 220 | 18.2 | 1.44 | 18.7 |
| 437 | 13.4 | | |

$^\Psi$Reactions were conducted at room temperature in 50 mM phosphate buffer (pH 6.0) in a final volume of 2.0 mL. MPO reactions were initiated by addition of 5 $\mu$L (0.5 $\mu$g) of HSMPO.
^assayed in the presence of 1.44 mM o-DA
⊥assayed in the presence of 300 $\mu$M $H_2O_2$ Example 2

To evaluate potential assay interference by ASC, conditions were selected which permitted the spectrophotometric assessment of ASC effects on the extent of o-DA oxidation. This was accomplished using sub-saturating concentrations of $H_2O_2$ (37 mM), 1.5 mM o-DA a nd excess enzyme. MPO activity was assayed at room temperature in a final volume of 3.0 mL containing 50 mM potassium phosphate buffer (pH 6.0), 37 mM $H_2O_2$, and 1.5 mM o-DA. Reactions were initiated by addition of 2 mg HSMPO: (a) control reaction, (b) ASC (3.2 mM) added 3.6 minutes after initiation of the reaction, (c) ASC (32 mM) added just prior to the initiation of the reaction and (d) ASC (64 mM) added just prior to the initiation of the reaction. The results are shown in FIG. 1. Under these conditions, the maximum change in 460 nm absorbance was attained within 1.5 minutes of enzyme addition, with minimal change in absorbance occurring thereafter. These results indicate that when ASC (32 mM) was present at the onset of the reaction, there was a reduction of approximately 50% in absorbance at 460 nm (FIG. 1c) compared to control reactions devoid of ASC (FIG. 1a). At an ASC concentration of 64 mM, (FIG. 1d) the development of absorbance at 460 nm was fully abolished. However, addition of ASC in great excess (i.e., 3.2 mM) to a control reaction when enzyme catalysis had ceased had little effect on the 460 nm absorbance attained (FIG. 1b). This small decrease in absorbance following ASC addition at the time of ceased catalysis was entirely attributable to the change in reaction volume upon addition of ASC.

Example 3

Figure 2:
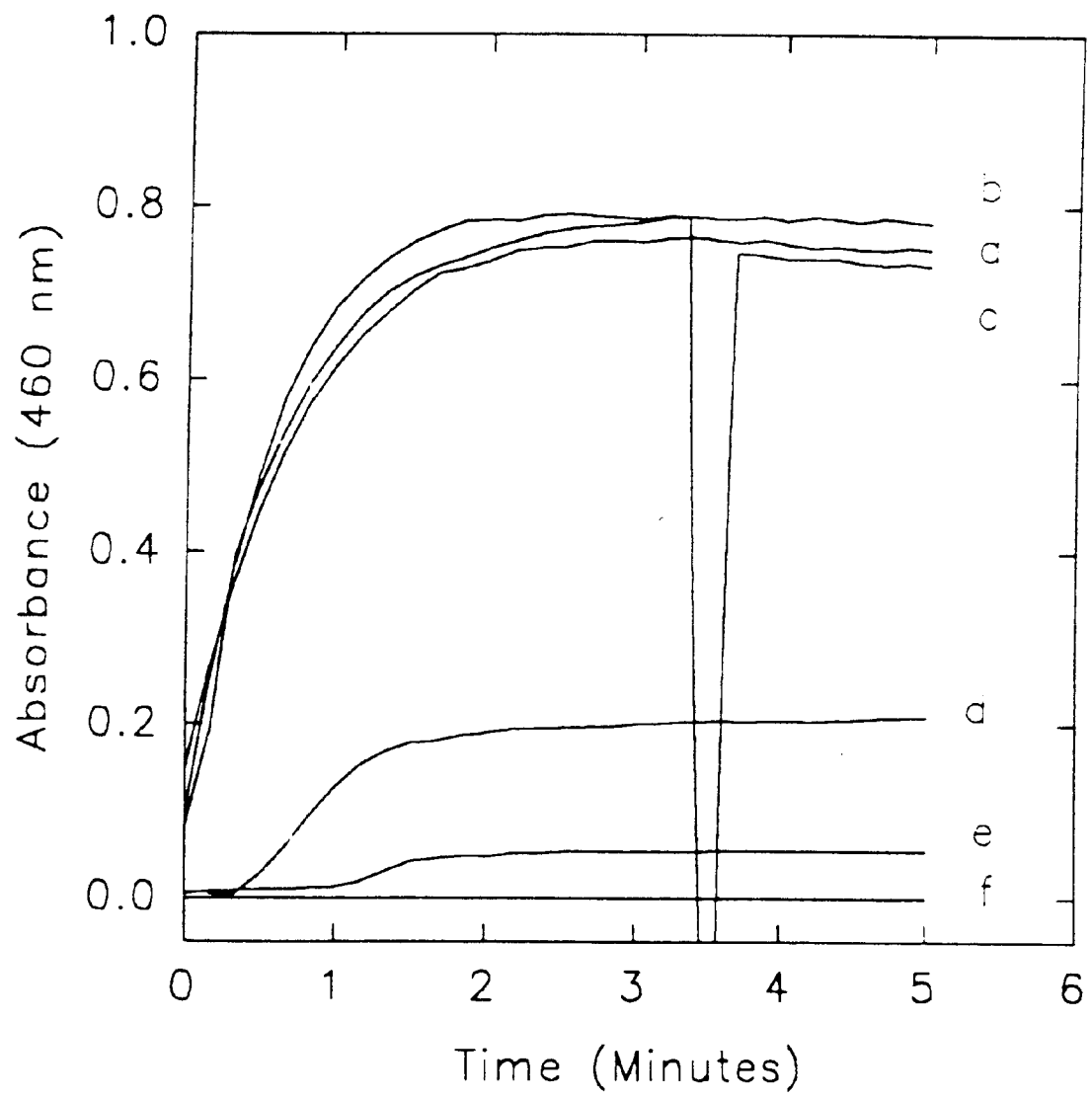
FIG. 2 shows the effect of GSH on MPO-catalyzed oxidation of o-DA.

The effect of GSH on o-DA oxidation by HSMPO was assessed in an analogous fashion. See FIG. 2. MPO activity was assayed at room temperature in 3.0 mL of 50 mM potassium phosphate (pH 6.0), supplemented with 37 mM $H_2O_2$, and 1.5 mM o-DA. (a) HSMPO (2 mg) was added 2 minutes after addition of NEM (6.6 mM) and GSH (1.65 mM), (b) NEM (6.6 mM) was added 5 minutes prior to addition of HSMPO (2 mg) (c) GSH (3.3 mM) was added 3.5 minutes after initiation of the reaction by addition of HSMPO (2 mg), (d) GSH (0.33 mM) was added just prior to initiation of the reaction with HSMPO (2 mg) with NEM (6.6 mM) added 20 seconds following initiation of the reaction, (e) GSH (0.33 mM) was added just prior to initiation of the reaction with HSMPO (2 mg) with NEM (6.6 mM) added 1.0 minute following initiation of the reaction, and (f) GSH (1.65 mM) was added just prior to initiation of the reaction. The results obtained were qualitatively similar to those observed with ASC. GSH (1.65 mM) fully prevented the increase in 460 nm absorbancy when present at the initiation of the MPO reaction with addition of enzyme (FIG. 2f). The inhibitory effect of GSH was fully abolished when NEM (6.6 mM) was added together with GSH to the reaction mixture 2 minutes prior to addition of enzyme (FIG. 2a). Addition of NEM to GSH (0.33 mM)-supplemented reactions already in progress (FIGS. 2d,e) resulted in increased final absorbance readings as the time interval between enzyme and NEM addition was shortened. Alone, NEM had little effect on MPO activity (FIG. 2b). As observed with ASC, addition of GSH to control peroxidase reactions that had ceased produced little change in absorbancy (FIG. 2c). This minimal change in absorbance was accounted for by the volume dilution with GSH addition.

These findings demonstrate that both ASC and GSH effectively interfere in the spectrophotometric assay of MPO by competing for o-DA as the hydrogen donor (peroxidase co-substrate) and in situ formation of 3,3'-dimethoxybenzidinediimine. See, Claiborne et al., *Biochemistry* 18: 2324–2329 (1979), and Wise et al., *Carcinogenesis* 6: 579–583 (1985). The interference by both ASC and GSH was concentration dependent, with ASC being more effective than GSH. There is no evidence, however, that either ASC or GSH reacted with the stable bisazobiphenyl condensation product dimer which forms from 3,3'-dimethoxybenzidine-diimine and apparently accumulates in ceased MPO reactions. See, Claiborne et al., *Biochemistry* 18: 2324–2329 (1979).

Example 4

A series of experiments was conducted to evaluate the recovery of MPO activity from PMNs entering the eyes of Lewis rats within 24 hours after a single subplantar administration of LPS. In these studies, interfering cytoplasmic components were extensively diluted during tissue homogenization and subsequently separated from the PMN-containing membranous tissue pellet by centrifugation. In addition, NEM was tested for its potential to enhance the recovery of PMN associated MPO activity by homogenizing the tissue in buffer supplemented with this sulfhydryl reagent.

A) As a control group, whole globes were obtained from unchallenged, saline injected animals. Following homogenization, the membranous pellet was washed with phosphate buffer (with or without added NEM), and then solubilized with HTA-Br containing buffer. These ocular tissue preparations yielded MPO activity ranging from 0.7 to 1.4 mM/min/100 mg (Table 2).

B) As shown in Table 2, recovery of ocular MPO activity from the endotoxin-treated animals varied considerably, depending on the extraction procedure employed. Challenged rats whose eyes were homogenized in the HTA-Br buffer alone exhibited moderately increased (10-fold) ocular MPO activity (10.9 mM/min/100 mg). Measurable ocular MPO activity was enhanced (42.1 mM/min/100 mg) when the final HTA-Br solubilization was preceded by tissue homogenization, centrifugation, and washing with 50 mM phosphate buffer. However, when NEM (10 mM) was included in the phosphate buffer, recovery of LPS-stimulated ocular MPO activity further increased to 106.6 mM/min/100 mg, indicating a 100-fold increase over the eyes from unchallenged animals.

TABLE 2

Effect of various tissue extractions on the recovery of ocular MPO activity following LPS administration in the Lewis rat

| Animal Treatment | Homogenization Buffer/Volume | | | MPO Activity $\mu$M/min/ 100 mg (x ± S.D.) (n = 10) |
|---|---|---|---|---|
| | Phosphate [50 mM] pH 7.4 | Phosphate/ NEM [50 mM/ 10 mM] pH 7.4 | HTA-Br^ pH 6.0 | |
| Saline | 2 × 5.0 mL | — | 1.0 mL | 0.7 ± 0.1 |
| Saline | — | 2 × 5.0 mL | 1.0 mL | 1.4 ± 0.4 |
| 200 $\mu$g LPSΨ | — | — | 0.5 mL | 10.9 ± 4.0 |
| 200 $\mu$g LPS | 2 × 5.0 mL | — | 0.5 mL | 42.1 ± 10.9 |
| 200 $\mu$g LPS | — | 2 × 5.0 mL | 0.5 mL | * 106.6 ± 35.2 * |

Ψsubplantar injection
^ HTA-Br Buffer = 0.5% HTA-Br/50 mM k-phosphate (pH 6.0)
*significantly different from LPS in HTA-Br alone (p < 0.01, t test)

Example 5

The substrate dependence on $H_2O_2$ and o-DA of MPO from eyes of LPS-stimulated animals was investigated (Table 3). Extraction with HTA-Br following tissue homogenization and washing with NEM-containing phosphate buffer (10 mM/50 mM, respectively) produced virtually identical results to those observed with the HSMPO (Table 1). Optimal reaction rates were attained in the presence of 180 to 300 mM $H_2O_2$ and 1.5 mM o-DA (Table 3). The similar substrate dependence observed for HSMPO and the MPO extracted from eyes of LPS-challenged animals indicates that tissue extraction with NEM-containing buffer had little effect on the kinetic properties of the enzyme.

TABLE 3

KineticsΨ of HTA-Br solubilized MPO activity from whole eyes of Lewis rats 24 hours post-endotoxin challenge in the foot pad

| $H_2O_2$ Concentration ($\mu$M) | Reaction Velocity^ ($\mu$M/min) | o-DA Concentration (mM) | Reaction Velocity⊥ ($\mu$M/min) |
|---|---|---|---|
| 0 | 0 | 0 | 0 |
| 16 | 11.0 | 0.15 | 9.0 |
| 32 | 21.1 | 0.30 | 16.3 |
| 62 | 35.0 | 0.59 | 27.4 |
| 93 | 42.7 | 0.89 | 36.2 |
| 124 | 46.7 | 1.18 | 45.3 |
| 182 | 51.8 | 1.46 | 53.1 |
| 241 | 52.2 | | |
| 298 | 51.8 | | |

ΨReactions were conducted at room temperature in 50 mM phosphate buffer (pH 6.0) in a final volume of 2.0 mL. MPO reactions were initiated by addition of 100 $\mu$L of NEM-treated/HTA-Br solubilized ocular tissue extract (⅕ of total extract) prepared from rat eyes 24 hours after subplantar bacterial endotoxin challenge (200 $\mu$g).
^assayed in the presence of 1.5 mM o-DA
⊥assayed in the presence of 300 $\mu$M $H_2O_2$

We claim:

1. An endotoxin-induced inflammation assay for evaluating a drug comprising the steps of:
   a) administering the drug to ocular tissue of an experimental animal;

b) inducing inflammation in the animal by administration of an endotoxin;

c) isolating the ocular tissue approximately 16–30 hours after administration of the endotoxin;

d) homogenizing the ocular tissue in a buffered composition comprising a non-interfering thiol reactive compound, wherein the buffered composition has a pH of about 5–8;

e) centrifuging the composition of step (d) to recover neutrophils (PMN) and myeloperoxidase (MPO) in a pellet;

f) solubilizing the pellet of step (e) in a buffered composition containing hexadecyltrimethylammonium bromide (HTA-Br) in order to release MPO from PMN azurophil granules, wherein the buffered composition has a pH of about 5–7;

g) centrifuging the composition of step (f) to recover MPO in the supernatant;

h) preparing a buffered composition comprising the supernatant of step (g), o-dianisidine (o-DA), $H_2O_2$ and HTA-Br, wherein the buffered composition has a pH of about 5–7, preferably about pH 6; and i) determining MPO activity by spectrophotometrically monitoring at about 460 nm change in absorbance of the composition of step (h) due to o-DA oxidation.

2. The assay of claim 1 wherein the non-interfering thiol reactive compound is selected from the group consisting of maleimide; N-methyl maleimide; N-ethyl maleimide; ethacrynic acid; and maleic anhydride.

3. The assay of claim 2 wherein the non-interfering thiol reactive compound is N-ethyl maleimide.

4. The assay of claim 1 wherein the buffer in the compositions of steps (d) and (f) is phopshate buffer, the composition of step (d) has a pH of about 7.4, and the composition of step (f) has a pH of about 6.

5. The assay of claim 1 wherein the ocular tissue is isolated in step (c) approximately 24 hours after administration of the endotoxin.

6. The assay of claim 1 wherein the centrifuging steps (e) and (g) are conducted at about 4° C.

7. The assay of claim 1 wherein the concentration of non-interfering thiol reactive compound in the composition of step (d) is about 0.1–30 mM.

8. The assay of claim 1 wherein the concentration of the non-interfering thiol reactive compound in the composition of step (d) is about 10 mM.

9. The assay of claim 1 wherein after step (e) and before step (f), the pellet is re-dissolved in a buffered composition comprising a non-interfering thiol reactive compound, wherein the buffered composition has a pH of about 5–8, and the resulting composition is centrifuged to recover PMN and MPO in a pellet.

10. The assay of claim 1 wherein the amount of o-DA in the composition of step (h) is about 1–1.5 mM, the amount of $H_2O_2$ is about 150–300 $\mu$M, and the amount of HTA-Br is about 100–500 $\mu$M.

11. The assay of claim 10 wherein the amount of o-DA in the composition of step (h) is about 1.4–1.5 mM, the amount of $H_2O_2$ is about 220–300 $\mu$M, and the amount of HTA-Br is about 250 $\mu$M.

12. The assay of claim 1 wherein the experimental animal is selected from the group consisting of Lewis rats; NZA rabbits; and DB rabbits.

* * * * *